US007783339B2

(12) United States Patent
Lee et al.

(10) Patent No.: US 7,783,339 B2
(45) Date of Patent: Aug. 24, 2010

(54) METHOD AND SYSTEM FOR REAL-TIME DIGITAL FILTERING FOR ELECTROPHYSIOLOGICAL AND HEMODYNAMIC AMPLIFERS

(75) Inventors: Samuel Lee, Brookfield, WI (US); Joel Q. Xue, Germantown, WI (US)

(73) Assignee: The General Electric Company, Schenectady, NY (US)

( * ) Notice: Subject to any disclaimer, the term of this patent is extended or adjusted under 35 U.S.C. 154(b) by 1034 days.

(21) Appl. No.: 11/467,361

(22) Filed: Aug. 25, 2006

(65) Prior Publication Data

US 2007/0265537 A1    Nov. 15, 2007

Related U.S. Application Data

(60) Provisional application No. 60/800,372, filed on May 15, 2006.

(51) Int. Cl.
 *A61B 5/04* (2006.01)
(52) U.S. Cl. ..................................................... 600/509
(58) Field of Classification Search ................ 600/509, 600/510, 484, 521; 607/2, 5, 7, 9
See application file for complete search history.

(56) References Cited

U.S. PATENT DOCUMENTS

| 4,944,299 A | 7/1990 | Silvian |
| 5,197,467 A | 3/1993 | Steinhaus et al. |
| 5,400,795 A | 3/1995 | Murphy et al. |
| 5,494,042 A | 2/1996 | Panescu et al. |
| 5,647,379 A | 7/1997 | Meltzer |
| 5,660,184 A * | 8/1997 | Donehoo et al. ............. 600/509 |
| 5,795,303 A | 8/1998 | Swanson et al. |
| 6,351,664 B1 | 2/2002 | Brodnick |
| 2003/0194030 A1* | 10/2003 | Modlin ....................... 375/346 |
| 2008/0103535 A1* | 5/2008 | Ostroff et al. .................. 607/2 |

FOREIGN PATENT DOCUMENTS

WO    03/043494 A1    5/2003

OTHER PUBLICATIONS

PCT International Search Report mailed May 29, 2008.
Database Inspec [Online] The Institution of Electrical Engineers, Stevenage, GB; Jan. 2006, Ramashri T. et al: "Data compression using FFT and digital filters in PCM telemetry applications". XP-00248052, Database accession No. 8918983 abstract.

* cited by examiner

*Primary Examiner*—George Manuel
*Assistant Examiner*—Robert N Wieland
(74) *Attorney, Agent, or Firm*—Andrus, Sceales, Starke & Sawall, LLP

(57) ABSTRACT

The present invention includes a method and system for real-time digital filtering for electrophysiological and hemodynamic amplifiers. The invention replaces the analog circuits currently used for signal filtering and conditioning in such systems with digital filters that may be implemented in a software application. The method and system includes digitizing the analog signal collected from the patient prior to performing the signal filtering and conditioning. The method and system also includes removing stimulus artifacts, as well as performing sample rate conversion and scaling on the digital signal. The processed digital signals may be used, displayed, saved and converted to analog signal thru digital-to-analog conversion.

15 Claims, 2 Drawing Sheets

METHOD AND SYSTEM FOR REAL-TIME DIGITAL FILTERING FOR ELECTROPHYSIOLOGICAL AND HEMODYNAMIC AMPLIFERS

RELATED APPLICATIONS

The present application is based on and claims priority to U.S. Provisional Patent Application Ser. No. 60/800,372, filed May 15, 2006.

FIELD OF THE INVENTION

The subject matter described herein relates to the field of invasive cardiology, and more particularly, to the field of signal filtering and conditioning.

BACKGROUND OF THE INVENTION

In the field of invasive cardiology, analog cardiac data is collected with heart catheters by electrophysiological and hemodynamic amplifiers and requires signal filtering and conditioning before it may be used. Current electrophysiological and hemodynamic amplifiers use cascaded analog circuits to perform signal filtering and conditioning. This signal filtering and conditioning is performed after analog anti-aliasing, but before analog-to-digital conversion. This (analog circuit based) signal filtering and conditioning process can be problematic, specifically, the amplified analog signals arc consistently noisy and have poor signal resolution due to imprecise analog components. In fact, the precision of the analog components is approximately 1%. Furthermore, the systems utilized to process these analog signals are often times inflexible due to the unadjustable nature of the analog circuits. Lastly, the analog amplifiers currently used make it difficult or even impossible to address application problems such as removal of pacing stimulus artifacts in the signal. What is needed is a method and system of real-time digital filtering for these amplifiers that produce better quality signals, flexibility in system stricture, and additional functionality such as removing pacing stimulus artifacts from the signal.

BRIEF DESCRIPTION OF THE INVENTION

A method and system for real-time digital filtering for electrophysiological and hemodynamic amplifiers is provided. The system replaces the analog circuits currently used in such systems for signal filtering and conditioning with digital filters that may be implemented in a software application. The method and system includes digitizing the analog signal collected from the patient prior to performing the signal filtering and conditioning. The method and system also includes removing stimulus artifacts, as well as performing sample rate conversion and scaling on the digital signal. The processed digital signals may be used, displayed, saved and converted to analog signal through digital-to-analog conversion.

In one embodiment a method of real-time digital filtering for electrophysiological and hemodynamic amplifiers comprises inputting a set of digital data from a patient, removing a stimulus artifact from the set of digital data when a pacing function is on, filtering the set of digital data with a first order high-pass filter and a second order low-pass filter or a special resonator, and performing a sample rate conversion and a data scaling on the set of digital data when a notch function is off. This method further comprises filtering the set of digital data with three first-order Butterworth notch filters at base, 2nd and 3rd harmonics of the power line frequency when the notch function is on, and the notch function is fixed, and filtering the set of digital data with three amplitude adaptive notch filters at base, 2nd and 3rd harmonics of the power line frequency when the notch function is on, and the notch function is not fixed, and collecting a set of analog cardiac data from the patient, and converting the analog cardiac data to the set of digital data wherein the first order high-pass filter and the second order low-pass filter are Butterworth type digital filers. The method further comprises outputting the set of digital data to an output device, converting the outputted set of digital data to an analog signal.

Another embodiment of a system for real-time digital filtering for electrophysiological and hemodynamic amplifiers is provided. The system comprises an acquisition device configured to collect a set of analog cardiac data from a patient, wherein the acquisition device is further configured to convert the set of analog cardiac data to a set of digital data, a storage media for storing a computer application and a processing unit coupled to the acquisition device and the storage media, the processing unit configured to execute the computer application, and further configured to receive the set of digital data from the acquisition device, wherein when the computer application is executed, a stimulus artifact is removed from the set of digital data when a pacing function is on, and the set of digital data is filtered with a first order high-pass filter and a second order low-pass filter or a special resonator, and a sample rate conversion and a data scaling is performed on the set of digital data when a notch function is off. The set of digital data is filtered with three first-order Butterworth notch filters at base, 2nd and 3rd harmonics of the power line frequency when the notch function is on, and the notch function is fixed, and the set of digital data is filtered with three amplitude adaptive notch filters at base, 2nd and 3rd harmonics of the power line frequency when the notch function is on, and the notch function is not fixed. The first order high-pass filter and the second order low-pass filter are Butterworth type digital filers. The system further comprises an output device configured to receive an outputted set of digital data wherein the outputted set of digital data is converted to an analog signal.

DETAILED DESCRIPTION

The method and system improves current electrophysiological and hemodynamic amplifiers by replacing cascaded analog filtering circuits with cascaded digital filters, which may be implemented in computer software for signal filtering and conditioning based on mathematical algorithms. Specifically, the analog high pass filter will be replaced with a digital high pass filter, the analog low pass filter with a digital low pass filter, and the analog fixed notch filters with digital fixed notch filters.

In addition, in order to improve removal of power line noise while preserving signal contents around the power line frequency and the corresponding $2^{nd}$ and $3^{rd}$ harmonics, users will have the option to select amplitude adaptive notch filtering; and in order to compensate for signal attenuation from analog anti-aliasing and analog-to-digital conversion, a digital special resonator will be used for signal boosting.

At the start of the electrophysiological and hemodynamic application, or when the user changes system configuration parameters that affect the digital filtering, filter coefficients are calculated and updated. Once a digital sample is output from the analog-to-digital converter, the sample data is removed of pacing stimulus artifacts if pacing is on, and processed by the high pass filter, then the low pass filter, or the special digital resonator depending on the user-selected low pass cutoff frequency, which determines signal attenuation from analog anti-aliasing and analog-to-digital conversion. The signal is then filtered by the notch filters, the fixed notch filters or amplitude adaptive notch filters depending on user's choice if notch is on, and finally the sample rate conversion and data scaling are performed before the sample is output.

New electrophysiological and hemodynamic amplifiers clearly solve the above three problems because they provide cleaner signals and better signal resolution since digital algorithms have better precision (0.0001% round-off error), flexible systems since digital filter coefficients can be easily calculated, and they have potential in addressing application problems such as removal of pacing stimulus artifacts by adding additional digital filtering algorithms.

Figure 1:
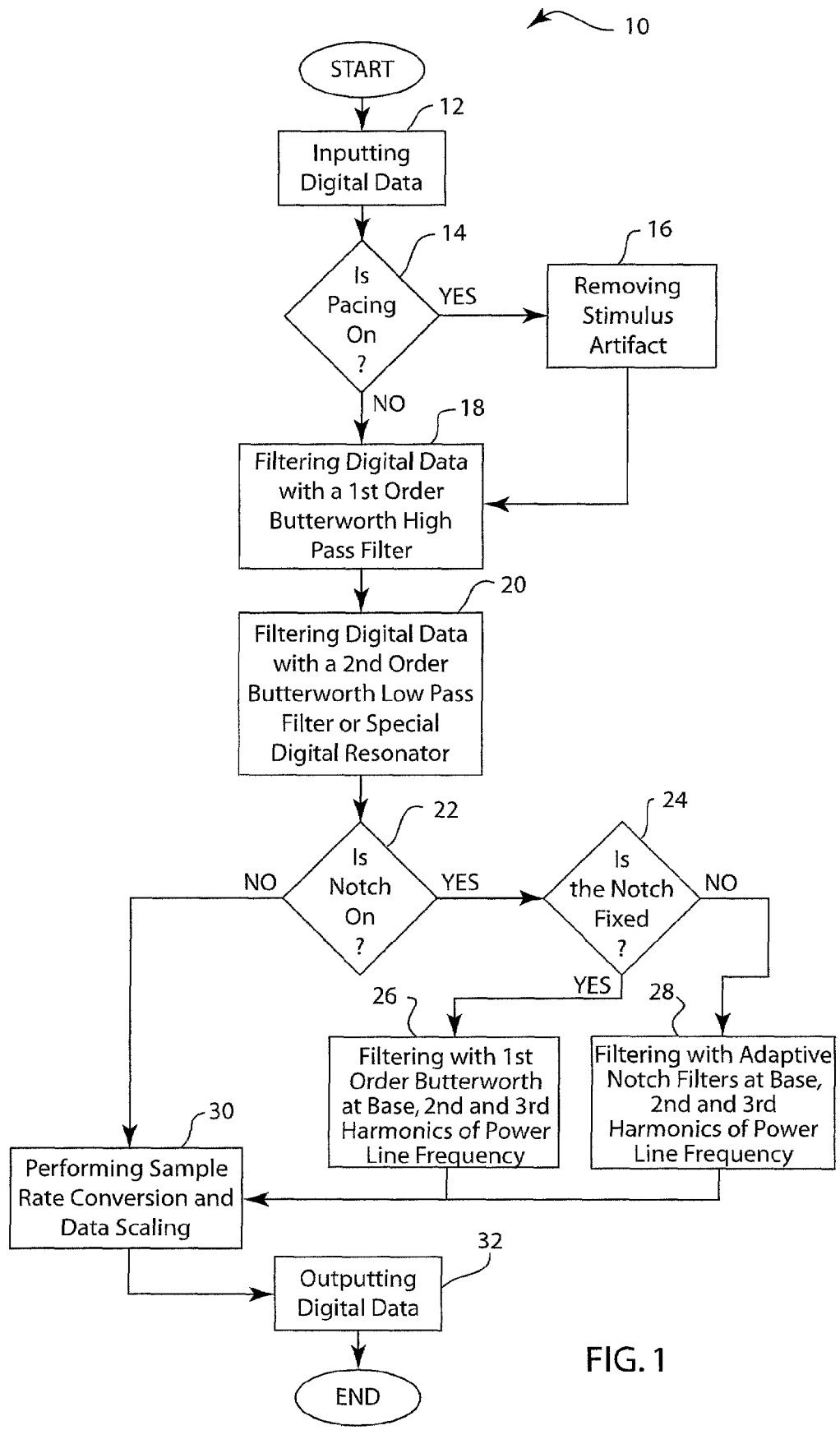
FIG. 1 shows a flow chart of an embodiment of a method of realtime digital filtering.

Referring to FIG. 1, an embodiment of a filtering method 10 of the present invention is depicted in the flow chart. After collecting the analog cardiac data from a patient with a catheter, the signal is digitized and the digital data is inputted in step 12. If a pacing function is on in step 14, the stimulus artifact is removed from the digital signal in step 16. Step 16 is performed by using exponential curve fitting for the pace noise, and then subtracting that portion from the digital signal. Before describing the subsequent steps of the filtering method 10, it is important to describe the various Butterworth filters utilized in this invention.

Butterworth High-pass, Low-Pass and Notch Filters

The transfer function $H(s)$ for the nth order Butterworth low-pass analog filter is generally given in Eq. A1 below:

$$H_{low\text{-}pass}(s) = \frac{1}{(1+s/\Omega_c)^\rho \prod_{k=1}^{[n/2]} \{1 + 2\sin[(2k-1)\pi/(2n)]s/\Omega_c + (s/\Omega_c)^2\}} \quad \text{Eq. A1}$$

Where $[n/2]$ is the integer part of $n/2$, $\rho=0$ or 1 depending on whether n is even or odd, $\Omega_c$ is the analog 3 dB cutoff frequency. This general formula gives an expression whose denominator is the product of $2^{nd}$ order polynomials in s. When n is odd, there is a $1^{st}$ order polynomials also.

Replacing $s/\Omega_c$ with $\Omega_c/s$ in above Eq. A1, we obtain the transfer function $H(s)$ for the nth order Butterworth high-pass analog filter:

$$H_{high\text{-}pass}(s) = \frac{1}{(1+\Omega_c/s)^\rho \prod_{k=1}^{[n/2]} \{1 + 2\sin[(2k-1)\pi/(2n)]\Omega_c/s + (\Omega_c/s)^2\}} \quad \text{Eq. A2}$$

From Equations A1-2, the transfer functions $H(z)$ for the nth order Butterworth low-pass and high-pass digital filters may be obtained by applying the following bilinear transformation:

$$s/\Omega_c = \frac{1-z^{-1}}{\tan(\pi f_c/f_s)(1+z^{-1})} \quad \text{Eq. A3}$$

Where $f_c$ is the 3 dB cutoff frequency in Hz of the low-pass or high-pass digital filter and $f_s$ is the sampling frequency in Hz.

Once the transfer function of a digital filter is obtained in the following format:

$$H(z) = \frac{\sum_{l=0}^{N-1} b_l z^{-l}}{\sum_{l=0}^{N-1} a_l z^{-l}} \quad \text{Eq. A4}$$

Where $a_l$, $b_l$ ($l=0$ to $N-1$) and N are a coefficients, b coefficients and the length or number of a or b coefficients of the filters ($a_0 \neq 0$).

The difference Eq. describing the output response $y_n$ to input sample $x_n$ of the filter is readily obtained (same as Eq. 1) below:

$$y_n = \left(\sum_{l=0}^{N-1} b_l x_{n-l} - \sum_{l=1}^{N-1} a_l y_{n-l}\right) / a_0 \quad \text{Eq. A5}$$

Finally, the transfer function $H(z)$ of the $1^{st}$ order Butterworth band-stop or notch digital filter is obtained by applying the following transformation to the transfer function of the $1^{st}$ order Butterworth low-pass digital filter:

$$z^{-1} = \frac{a_2 - a_1 z^{-1} + z^{-2}}{1 - a_1 z^{-1} + a_2 z^{-2}} \quad \text{Eq. A6}$$

Where, $$a_1 = 2\alpha/(k+1) \quad \text{Eq. A6i}$$

$$a_2 = (1-k)/(k+1) \quad \text{Eq. A6ii}$$

$$\alpha = \cos(\pi(f_u+f_l)/f_s)/\cos(\pi(f_u-f_l)/f_s) \quad \text{Eq. A6iii}$$

$$k = \tan(\pi(f_u-f_l)/f_s)\tan(\pi f_c/f_s) \quad \text{Eq. A6iv}$$

($f_c$=the 3 dB cutoff frequency in Hz of the original low-pass filter, $f_u$, $f_l$=upper, lower 3 dB cutoff frequencies in Hz of the new notch filter and $f_s$=sampling rate in Hz).

Referring back to FIG. 1, in step 18, the digital data is filtered with a first order Butterworth high-pass filter. The specific operation of the first order Butterworth high-pass filter is described below:

$1^{st}$ Order Butterworth High-Pass IIR Filter

The mathematical formula for $1^{st}$ order Butterworth high-pass IIR digital filter is illustrated below:

$$y_n = b_0 x_n + b_1 x_{n-1} - a_1 y_{n-1} \quad \text{Eq. A7}$$

Where, $$b_0 = 1/(k+1) \quad \text{Eq. A7i}$$

$$b_1 = -b_0 \quad \text{Eq. A7ii}$$

$$a_1=(k-1)/(k+1) \qquad \text{Eq. A7iii}$$

$$k=\tan(\pi f_c/f_s) \qquad \text{Eq. A7iv}$$

($f_c$=3 dB cutoff frequency in Hz and $f_s$=sampling rate in Hz).

In step 20, the digital data is then filtered with a second-order Butterworth low-pass filter or a special digital resonator. A detailed description of the $2^{nd}$ order Butterworth low-pass filter is included below as well.

2nd Order Butterworth Low-Pass IIR Filter

The mathematical formula for $2^{nd}$ order Butterworth low-pass IIR digital filter is illustrated below:

$$y_n=b_0x_n+b_1x_{n-1}+b_2x_{n-2}-a_1y_{n-1}-a_2y_{n-2} \qquad \text{Eq. A8}$$

Where, $$b_0=k^2/(k^2+\sqrt{2}k+1)) \qquad \text{Eq. A8i}$$

$$b_1=2b_0 \qquad \text{Eq. A8ii}$$

$$b_2=b_0 \qquad \text{Eq. A8iii}$$

$$a_1=2(k^2-1)/(k^2+\sqrt{2}k+1) \qquad \text{Eq. A8v}$$

$$a_2=(k^2-\sqrt{2}k+1)/(k^2+\sqrt{2}k+1) \qquad \text{Eq. A8vi}$$

$$k=\tan(\pi f_c/f_s) \qquad \text{Eq. A8viii}$$

($f_c$=3 dB cutoff frequency in Hz and $f_s$ sampling rate in Hz).

Still referring to FIG. 1, if the notch function is off in step 22, then a sample rate conversion and data scaling of the digital data is performed in step 30. The system and method will utilize the Shannon's sampling theorem to reconstruct the signal from its digital original samples, at the original sample rate, and then resample it at the output sampling rate. This type of sample rate conversion will incorporate anti-aliasing before down sampling and remove duplicate spectra after up-sampling after step 30, the digital data will be outputted in step 32. The digital data may be outputted to a digital to analog converter so that it may be relayed onto a monitor, monitoring system, or any type of physician workstation or physician device. Likewise, the outputted digital signal may be utilized without conversion to analog.

Referring back to step 22 of FIG. 1, if the notch function is on, then in step 24, it will be determined whether the notch is fixed. If the notch is fixed, then the digital data will be filtered with a first order Butterworth notch filter at the base in step 26. The specifics of this filtering method are shown below.

$1^{st}$ Order Butterworth Band-Stop (Notch) IIR Filter

The mathematical formula for $1^{st}$ order Butterworth band-stop (notch) IIR digital filter is illustrated below:

$$y_n=b_0x_n+b_1x_{n-1}+b_2x_{n-2}-a_1y_{n-1}-a_2y_{-2} \qquad \text{Eq. A9}$$

Where, $$b_0=1/(1+\beta) \qquad \text{Eq. A9i}$$

$$b_1=2\alpha/(1+\beta) \qquad \text{Eq. A9ii}$$

$$b_2=b_0 \qquad \text{Eq. A9iii}$$

$$a_1=b_1 \qquad \text{Eq. A9iv}$$

$$a_2=(1-\beta)/(1+\beta) \qquad \text{Eq. A9v}$$

$$\alpha=\cos(\pi(f_u+f_l)/f_s)/\cos(\pi(f_u-f_l)/f_s) \qquad \text{Eq. A9vi}$$

$$\beta=\tan(\pi(f_u-f_l)/f_s) \qquad \text{Eq. A9vii}$$

($f_u$, $f_l$=upper, lower 3 dB cutoff frequencies in Hz and $f_s$=sampling rate in Hz).

After the filtering step of step 26, the method will continue to step 30.

Referring back to step 24 of FIG. 1, if the notch is not fixed, then the method continues on to step 28, where the digital data is filtered with adaptive notch filters at the base. A detailed description of step 28 is outlined below.

Amplitude Adaptive Notch Filters with Power Line Frequency Detection

These filters have two portions: 1) detection of base power line and its harmonic frequencies; 2) adaptive amplitude filter using modeling technique.

In quite a few countries, the frequency of power line is not very stable due to poor load control, where the frequency can be higher when load is low, and frequency can be lower when load is high. In this way, a fixed power line frequency notch filter may not be able to reduce the noise to acceptable level. The new filter scan a segment of the data and perform power spectrum analysis to detect the spectrum peak around 50 Hz and 60 Hz depend on the presetting of the regional code. A threshold is set to a 3 times of standard deviation of the power spectrum of the surrounding region. If the power spectrum is exceeding this threshold, the location of the peak value is detected as notch filter frequency.

After the base frequency $f_p$ is detected, the $2^{nd}$ and $3^{rd}$ harmonic spectrum peaks are compared to the surrounding spectrum with the same 3 times standard deviation rule. If the spectrum peak exceeds the threshold, the harmonic notch filter(s) are set for the detected frequency. Otherwise, the harmonic filters are turned off to save the computation time.

The adaptive amplitude filter is to model the sinusoid signal first and then subtract the filter from the signal. A trigonometric identity $\sin(a+b)=2\sin(a)\cos(b)-\sin(a-b)$. That lead to the time series sinusoid signal model as: $s(n+1)=2*C*s(n)-s(n-1)$, where $C=\cos(2\pi f/fs)$, f=sinusoid signal frequency, fs is the sample frequency. In the real-time filtering, signal $s(n+1)$ need to be adapted to correct modeling error after the first estimation. A small constant is added to or subtracted from the estimated $s(n+1)$ depending on the polarity of the signal difference.

The mathematical formula for Amplitude Adaptive Notch Filter is illustrated below:

$$y_n=x_n-h_n \qquad \text{Eq. A12}$$

Where $h_n$ is the amplitude of power line interference noise at notch frequency, i.e., the power line base, $2^{nd}$ harmonic or $3^{rd}$ harmonic frequency. This $h_n$ is calculated from its past two points using the following formula:

$$h_n=ch_{n-1}-h_{n-2} \qquad \text{Eq. A13}$$

Where, $$c=2\cos(2\pi f_p/f_s) \qquad \text{Eq. A13i}$$

is notch frequency dependent coefficient ($f_p$=notch frequency in Hz and $f_s$=sampling rate in Hz).

Finally, the signal amplitude difference between the current and last sample is checked in order to provide a better estimate of the amplitude of the power line interference noise for next point using the following formula:

$$h_n+=\delta_a \text{ If } y_n>y_{n-1} \qquad \text{Eq. A14a}$$

$$h_n-=\delta_a \text{ If } y_n<y_{n-1} \qquad \text{Eq. A14b}$$

Where $\delta_a$ is the pre-configured amplitude adaptive step size.

After the filtering step is completed in step 28, the method continues on to step 30.

Figure 2:
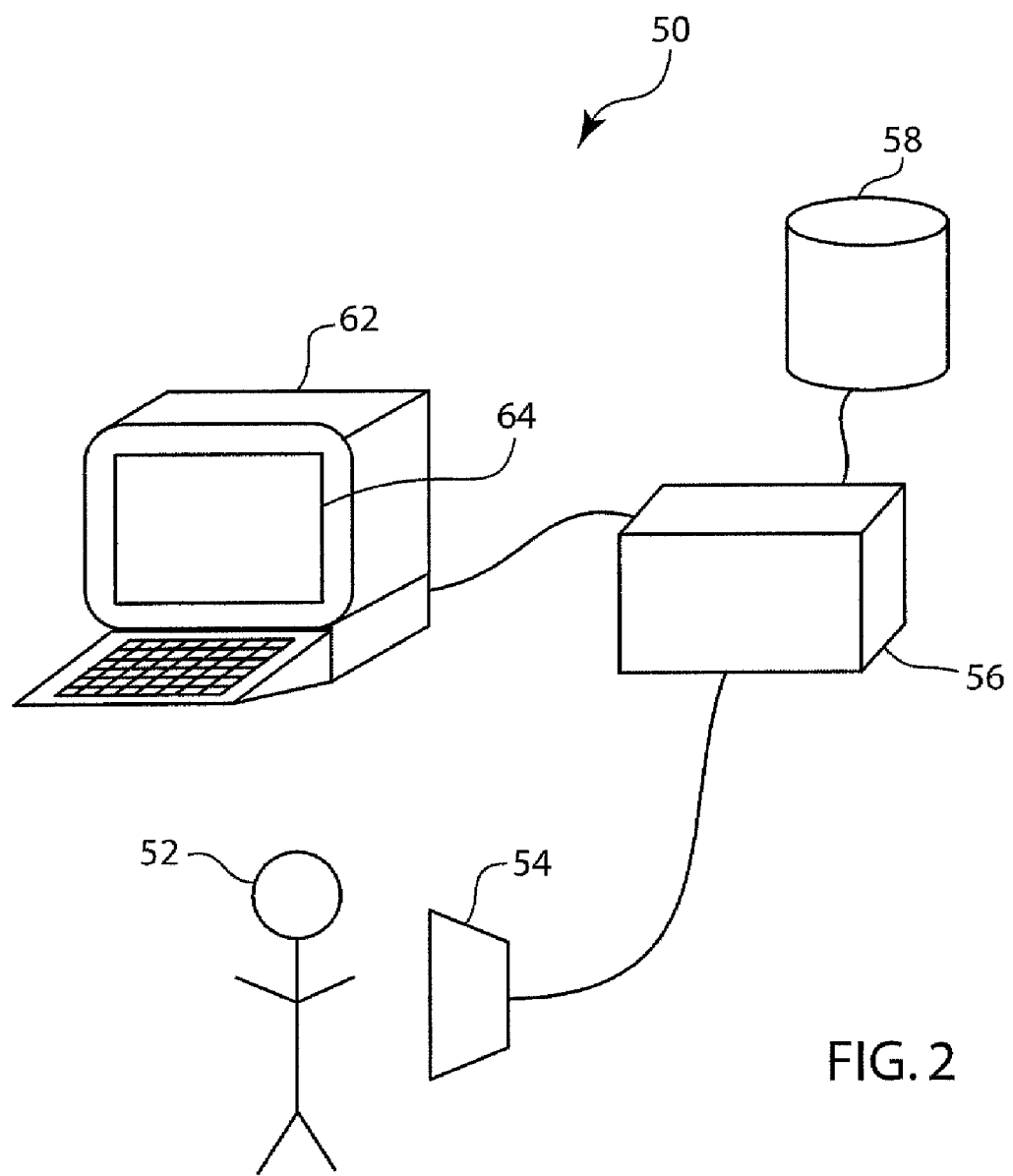
FIG. 2 illustrates a block diagram of an embodiment of a system for real-time digital filtering.

Referring now to FIG. 2, an embodiment of the system 50 of the present invention is depicted in the block diagram. It should be noted that the method as discussed above in FIG. 1 may be implemented as a software application and executed by the system 50, herein described with respect to FIG. 2. Referring now to FIG. 2, an embodiment of the system 50 of the present invention includes an acquisition device 54 configured to obtain a set of cardiac data from a patient 52. The acquisition device 54 is further configured to convert the analog data into digital data and relay the digital data to the processor 56. The storage media 58 in FIG. 2 includes the computer code embodying the software configured to carry out the method as described above. Executing the computer code, the processor performs the method on the collected digital data from the acquisition device 54 and provides the digital data output as described above in the method of FIG. 1 a technical effect of the system 50 is output of the digital data to the output device 62 for display on a graphical user interface 64 if desired. As noted above, the output device 62 may be any digital or analog device used to view, measure, manipulate or record such cardiac data. In the case of the output device 62 being an analog type device, a digital to analog converter will be utilized to convert the output data from the processor 56.

The electrophysiological and hemodynamic amplifiers of the present invention have three major advantages in that the digital filtering algorithms are much less bulky than analog filter circuits, there is a much lower cost in manufacturing with free duplication of digital algorithms versus the costly analog component, and the present invention is a flexible and extendable system capable of adding features and addressing application problems by using additional digital algorithms.

By replacing analog filtering circuits with real-time digital filtering, new electrophysiological and hemodynamic amplifiers provide cleaner signals and better signal resolution, flexibility and extensibility in signal filtering and conditioning, and makes solving some tough technical problems such as removal of pacing stimulus artifacts possible.

The present invention has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of real-time digital filtering for electrophysiological and hemodynamic amplifiers, the method comprising:
   inputting a set of digital data from a patient;
   removing a stimulus artifact from the set of digital data when a pacing function is on;
   filtering the set of digital data with a first order high-pass filter and a second order low-pass filter or a special resonator; and
   performing a sample rate conversion and a data scaling on the set of digital data when a notch function is off, wherein the sample rate conversion includes reconstructing the set of digital data from a set of original samples at an original sample rate, and further wherein the reconstructed set of digital data is resampled at an output sampling rate.

2. The method as claimed in claim 1, further comprising filtering the set of digital data with three first-order Butterworth notch filters at base, 2nd and 3rd harmonics of the power line frequency when the notch function is on, and the notch function is fixed.

3. The method as claimed in claim 1, further comprising filtering the set of digital data with three amplitude adaptive notch filters at base, 2nd and 3rd harmonics of the power line frequency when the notch function is on, and the notch function is not fixed.

4. The method as claimed in claim 1, further comprising collecting a set of analog cardiac data from the patient, and converting the analog cardiac data to the set of digital data.

5. The method as claimed in claim 1, wherein the first order high-pass filter and the second order low-pass filter are Butterworth type digital filters.

6. The method as claimed in claim 1, further comprising outputting the set of digital data to an output device.

7. The method as claimed in claim 6, further comprising converting the outputted set of digital data to an analog signal.

8. The method as claimed in claim 1, further comprising storing the set of digital data in a storage medium.

9. A system for real-time digital filtering for electrophysiological and hemodynamic amplifiers, the system comprising:
   an acquisition device configured to collect a set of analog cardiac data from a patient, wherein the acquisition device is further configured to convert the set of analog cardiac data to a set of digital data;
   a storage media for storing a computer application; and
   a processing unit coupled to the acquisition device and the storage media, the processing unit configured to execute the computer application, and further configured to receive the set of digital data from the acquisition device,
   wherein when the computer application is executed, a stimulus artifact is removed from the set of digital data when a pacing function is on, and the set of digital data is filtered with a first order high-pass filter and a second order low-pass filter or a special resonator, and a sample rate conversion and a data scaling is performed on the set of digital data when a notch function is off, wherein the sample rate conversion includes reconstructing the set of digital data from a set of original samples at an original, sample rate, and further wherein the reconstructed set of digital data is resampled at an output sampling rate.

10. The system as claimed in claim 9, wherein the set of digital data is filtered with three first-order Butterworth notch filters at base, 2nd and 3rd harmonics of the power line frequency when the notch function is on, and the notch function is fixed.

11. The system as claimed in claim 9, wherein the set of digital data is filtered with three amplitude adaptive notch filters at base, 2nd and 3rd harmonics of the power line frequency when the notch function is on, and the notch function is not fixed.

12. The system as claimed in claim 9, wherein the first order high-pass filter and the second order low-pass filter are Butterworth type digital filers.

13. The system as claimed in claim 9, further comprising an output device configured to receive an outputted set of digital data.

14. The system as claimed in claim 13, wherein the outputted set of digital data is converted to an analog signal.

15. A method of real-time digital filtering, the method comprising:

collecting a set of analog cardiac data from a patient;
converting the analog cardiac data to a set of digital data;
removing a stimulus artifact from the set of digital data when a pacing function is on;
filtering the set of digital data with a first order Butterworth high-pass filter and a second order Butterworth low-pass filter or a special resonator;
performing a sample rate conversion and a data scaling on the set of digital data when a notch function is off, wherein the sample rate conversion includes reconstructing the set of digital data from a set of original samples at an original sample rate, and further wherein the reconstructed set of digital data is resampled at an output sampling rate;
filtering the set of digital data with three first-order Butterworth notch filters at base, 2nd and 3rd harmonics of the power line frequency when the notch function is on, and the notch function is fixed;
filtering the set of digital data with three amplitude adaptive notch filters at base, 2nd and 3rd harmonics of the power line frequency when the notch function is on, and the notch function is not fixed; and
outputting an analog signal derived from the set of digital data.

* * * * *